United States Patent [19]

Szymczak

[11] Patent Number: 5,622,709

[45] Date of Patent: Apr. 22, 1997

[54] CIMETIDINE-PHENOL PHARMACEUTICAL COMPOSITION

[75] Inventor: Margaret M. Szymczak, Cherry Hill, N.J.

[73] Assignee: SmithKline Beecham Corporation, Philadelphia, Pa.

[21] Appl. No.: 491,897

[22] PCT Filed: Jan. 21, 1994

[86] PCT No.: PCT/US94/00807

§ 371 Date: Jul. 17, 1995

§ 102(e) Date: Jul. 17, 1995

[87] PCT Pub. No.: WO94/16695

PCT Pub. Date: Aug. 4, 1994

[51] Int. Cl.⁶ .......................... A61F 2/02; A61K 31/415; A61K 31/045

[52] U.S. Cl. .......................... 424/423; 514/400; 514/728

[58] Field of Search .......................... 514/400, 728; 424/423

[56] References Cited

U.S. PATENT DOCUMENTS 4,024,271  5/1977  Durant et al. .......................... 514/400

OTHER PUBLICATIONS

"Remington's Pharmaceutical Sciences", (15th ed.), Published 1982 by Mack (Easton, P.A.), p. 1466, col. 1, last paragraph.

*Primary Examiner*—Carlos Azpuru
*Attorney, Agent, or Firm*—Stephen Venetianer; Edward T. Lentz

[57] ABSTRACT

A parenteral dosage form for cimetidine is provided. The dosage form contains less phenol than conventional formulations.

2 Claims, No Drawings

CIMETIDINE-PHENOL PHARMACEUTICAL COMPOSITION

This application is a 371 of PCT/US94/00807 filed Jan. 21, 1994.

This invention relates to a parenteral dosage form comprising cimetidine, (as the HCl salt) phenol and water and to a method for the preparation of such a dosage form.

Cimetidine is a histamine H2-antagonist which has been described in U.K. Patent Specification 1,397,436, U.S. Pat. Nos. 3,950,233 and 4,024,271 and has the chemical name N"-cyano-N-methyl-N'-[2-[[(5-methyl-1 H-imidazol-4-yl)methyl]thio]-ethyl]-guanidine. Cimetidine has been shown to be useful in the treatment of duodenal, gastric, recurrent and stomal ulceration, and reflux esophagitis and in the management of patients who are at high risk from hemorrhage of the upper gastro-intestinal tract.

Cimetidine is currently manufactured as a 2 ml. single dose vial and an 8 ml. multiple dose vial solution with 0.5% w/v phenol as the preservative. It has now been found that a parenteral dose formulation of cimetidine with phenol and water can be prepared with the concentration of phenol being from about 0.1% to about 0.3% w/v. This reduction in phenol content results in a formulation that is equally effective as the prior art formulations without compromising the preservative effect of the phenol.

DETAILED DESCRIPTION OF THE INVENTION

This invention provides for a parenteral pharmaceutical dosage form comprising (i) cimetidine; (as the HCl salt)

(ii) phenol and (iii) water

The cimetidine will be present in an amount from about 300 mgs per 2 mls. per dosage form.

Phenol will be present in an amount of from about 0.1% to about 0.3% on a weight per volume basis.

The multiple dose vial solution of this invention is prepared by adding cimetidine hydrochloride to water and mixing thoroughly until dissolved. Phenol USP is added to the water and mixed thoroughly until dissolved. Sufficient Water for injection USP is added to bring solution up to final weight and mixed until homogeneous. Water for Injection is water purified by distillation or by reverse osmosis. It contains no added substance.

The pharmaceutical forms of this invention are present as ampules, single dose or multidose vials which are suitable for parenteral injection, for example, intravenous, subcutaneous or intramuscular administration.

Advantageously, equal doses will be administered one to four times a day.

The following example is not limiting but is merely illustrative of the compositions of this invention.

EXAMPLE ONE

A preparation which contains 1.511 kilograms of cimeticline HCl for parenteral injection was prepared in the following manner. 1.511 kilograms of cimetidine HCl were dissolved in 8.7 kgs of water. 26.4 grams of phenol were added to the resulting solution and 0.43 kgs of water were added to bring to final weight and volume and stirred well. The solution is filtered and aseptically filled into vials and stoppered.

What is claimed is:

1. A pharmaceutical composition which comprises (a) cimetidine HCl (b) about 0.1% to about 0.3% of phenol (c) Water of Injection.

2. A pharmaceutical composition according to claim 1 wherein the cimetidine HCl is present in an amount of about 300 mgs per 2 mls of water.

* * * * *